US009079858B2

(12) United States Patent
Alen et al.

(10) Patent No.: US 9,079,858 B2
(45) Date of Patent: *Jul. 14, 2015

(54) ROCK KINASE INHIBITORS

(75) Inventors: Jo Alen, Diepenbeek (BE); Sandro Boland, Diepenbeek (BE); Arnaud Pierre Jean Bourin, Diepenbeek (BE); Olivier Defert, Diepenbeek (BE); Dirk Leysen, Diepenbeek (BE)

(73) Assignee: Amakem NV, Diepenbeek (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/241,092

(22) PCT Filed: Aug. 31, 2012

(86) PCT No.: PCT/EP2012/067016
§ 371 (c)(1),
(2), (4) Date: Feb. 26, 2014

(87) PCT Pub. No.: WO2013/030365
PCT Pub. Date: Mar. 7, 2013

(65) Prior Publication Data
US 2014/0228408 A1    Aug. 14, 2014

(30) Foreign Application Priority Data

Aug. 31, 2011  (EP) .................................. 11179491

(51) Int. Cl.
| | |
|---|---|
| C07D 213/00 | (2006.01) |
| C07D 213/79 | (2006.01) |
| C07D 213/74 | (2006.01) |
| A61K 31/44 | (2006.01) |
| A61K 31/443 | (2006.01) |
| C07D 213/75 | (2006.01) |
| C07D 405/12 | (2006.01) |
| C07D 413/12 | (2006.01) |
| C07D 401/12 | (2006.01) |
| C07D 417/12 | (2006.01) |
| C07D 409/12 | (2006.01) |

(52) U.S. Cl.
CPC .............. *C07D 213/74* (2013.01); *A61K 31/44* (2013.01); *A61K 31/443* (2013.01); *C07D 213/75* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
CPC ...................................................... C07D 213/75
USPC ................................................. 546/309, 263
See application file for complete search history.

(56) References Cited

U.S. PATENT DOCUMENTS

| | | |
|---|---|---|
| 4,997,834 A | 3/1991 | Muro et al. |
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |
| 2009/0233960 A1 | 9/2009 | Van Rompaey et al. |
| 2014/0228408 A1 | 8/2014 | Alen et al. |

FOREIGN PATENT DOCUMENTS

| | | | |
|---|---|---|---|
| EP | 0370498 A2 | 11/1989 | |
| EP | 0721331 B1 | 9/1994 | |
| WO | 2007006546 A1 | 1/2007 | |
| WO | 2007006547 A1 | 1/2007 | |
| WO | 2007042321 * | 4/2007 | ........... C07D 213/40 |
| WO | 2007042321 A2 | 4/2007 | |
| WO | WO 2007042321 * | 4/2007 | ........... C07D 213/40 |
| WO | 2011107608 A1 | 9/2011 | |

OTHER PUBLICATIONS

West (Solid-State Chemistry and Its Applications, 1984, John Wiley & Sons.*
Loge et al., "Rho-kinase Inhibitors: Pharmacomodulations on the Lead Compound Y-32885", Journla of Enzyme Inhibition and Medicinal Chemistry, vol. 17, No. 6, pp. 381-390, Jan. 1, 2002.
European Search Report for Application No. 11179491.3 dated Nov. 30, 2011.

(Continued)

*Primary Examiner* — Nizal Chandrakumar
(74) *Attorney, Agent, or Firm* — Dinsmore & Shohl LLP

(57) ABSTRACT

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including sexual dysfunction, inflammatory diseases, ophthalmic diseases and respiratory diseases.

8 Claims, No Drawings

(56) References Cited

OTHER PUBLICATIONS

Search Report for International Application No. PCT/EP2012/067016 dated Nov. 29, 2012.
Search Report for International Application No. PCT/EP2012/067017 dated Nov. 5, 2012.
Search Report for International Application No. PCT/EP2012/067018 dated Nov. 5, 2012.
Office Action dated Jan. 7, 2015 pertaining to U.S. Appl. No. 14/241,096.
Office Action mailed Oct. 31, 2014 from U.S. Appl. No. 14/241,093.
Unpublished U.S. Appl. No. 14/241,096, filed Feb. 26, 2014.
Preliminary Amendment from U.S. Appl. No. 14/241,096, filed Feb. 26, 2014.
West, A., Solid State Chemistry and Its Applications; 1984, John Wiley & Sons.
Sagawa, H., et al., A Novel ROCK Inhibitor, Y-39983, Promotes Regeneration of Crushed Axons of Retinal Ganglion Cells Into the Optic Nerve of Adult Cats, ScienceDirect, Experimental Neurology, p. 230-240, 2005.
Hirata, A., et al., Y-27632, A Rho-Associated Protein Kinase Inhibitor, Attenuates Neuronal Cell Death After Transietn Retinal Ischemia, Graefes Arc Clin Exp Ophthalmol, vol. 246, p. 51-59, 2008, Japan.
Arita, R., et al., ROCK As a Therapeutic Target of Diabetic Retinopathy, Journal of Ophthalmology, vol. 2010, Article ID 175163, p. 1-9, Hindawi Publishing Corporation, 2010, http://www.hindawi.com.
Election Restriction Requirement pertaining to U.S. Appl. No. 14/241,096 dated Oct. 14, 2014.
Notice of Allowance dated Mar. 3, 2015 pertaining to U.S. Appl. No. 14/241,093.
Office Action dated Apr. 17, 2015 pertaining to U.S. Appl. No. 14/241,096.

\* cited by examiner

ROCK KINASE INHIBITORS

FIELD OF THE INVENTION

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease.

BACKGROUND OF THE INVENTION

The serine/threonine protein kinase ROCK consists in humans of two isoforms ROCK I and ROCK II. ROCK I is encoded on chromosome 18 whereas ROCK II, also called Rho-kinase, is located on chromosome 12. They both have a molecular weight close to 160 kDa. They share an overall homology of 65% while being 95% homologous in their kinase domains. Despite their sequence similarity, they differ by their tissue distributions. The highest levels of expression for ROCK I are observed in heart, lung and skeletal tissues whereas ROCK II is mostly expressed in brain. Recent data indicate that these two isoforms are partially function redundant, ROCK I being more involved in immunological events, ROCK II in smooth muscle function. The term ROCK refers to ROCK I (ROK-β, p160ROCK, or Rho-kinase β) and ROCK II (ROCK-α or Rho-kinase α).

ROCK activity has been shown to be enhanced by GTPase RhoA that is a member of the Rho (Ras homologous) GTP-binding proteins. The active GTP-bound state of RhoA interacts with Rho-binding domain (RBD) of ROCK that is located in an autoinhibitory carboxyl-terminal loop. Upon binding, the interactions between the ROCK negative regulatory domain and the kinase domain are disrupted. The process enables the kinase to acquire an open conformation in which it is fully active. The open conformation is also induced by the binding of lipid activators such as arachidonic acid to the PH domain in the kinase carboxyl-terminal domain. Another activation mechanism has been described during apoptosis and involves the cleavage of carboxyl terminus by caspase-3 and -2 (or granzyme B) for ROCK I and II, respectively.

ROCK plays an important role in various cellular functions such as smooth muscle contraction, actin cytoskeleton organization, platelet activation, downregulation of myosin phosphatase cell adhesion, -migration, -proliferation and survival, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, wound healing, cell transformation and gene expression. ROCK also acts in several signaling pathways that are involved in auto-immunity and inflammation. ROCK has been shown to play a part in the activation of NF-κB, a critical molecule that leads to the production of TNF and other inflammatory cytokines. ROCK inhibitors are reported to act against TNF-alpha and IL-6 production in lipopolysaccharide (LPS)-stimulated THP-1 macrophages. Therefore, ROCK inhibitors provide a useful therapy to treat autoimmune and inflammatory diseases as well as oxidative stress.

In conclusion, ROCK is a major control point in smooth muscle cell function and a key signaling component involved in inflammatory processes in various inflammatory cells as well as fibrosis and remodeling in many diseased organs. In addition, ROCK has been implicated in various diseases and disorders including eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythematosus, spasm, hypertension, chronic obstructive bladder disease, premature birth, infection, allergy, obesity, pancreatic disease and AIDS.

ROCK appears to be a safe target, as exemplified by knockout models and a large number of academic studies. These KO mice data, in combination with post-marketing surveillance studies with Fasudil, a moderately potent ROCK inhibitor used for the treatment of vasospasm after subarachnoid hemorrhage, indicate that ROCK is a genuine and significant drug target.

ROCK inhibitors would be useful as therapeutic agents for the treatment of disorders implicated in the ROCK pathway. Accordingly, there is a great need to develop ROCK inhibitors that are useful in treating various diseases or conditions associated with ROCK activation, particularly given the inadequate treatments currently available for the majority of these disorders. Some non-limiting examples include eye diseases (Age-related macular degeneration (dry or wet AMD), diabetic retinopathy, uveitis, glaucoma), or respiratory diseases (asthma, COPD . . . ).

Several different classes of ROCK inhibitors are known. The current focus is oncology and cardiovascular applications. Until now, the outstanding therapeutic potential of ROCK inhibitors has only been explored to a limited extent, because ROCK is such a potent and widespread biochemical regulator, that systemic inhibition of ROCK leads to strong biological effects that are considered as being side effects for the treatment of most of the diseases. Indeed, the medical use of ROCK inhibitors for non-cardiological indications is hampered by the pivotal role of ROCK in the regulation of the tonic phase of smooth muscle cell contraction. Systemically available ROCK inhibitors induce a marked decrease in blood pressure. Therefore, ROCK inhibitors with different properties are highly required.

For the target specific treatment of disorders by regulating smooth muscle function and/or inflammatory processes and/or remodeling, it is highly desired to deliver a ROCK inhibitor to the target organ and to avoid significant amounts of these drugs to enter other organs. Therefore, local or topical application is desired. Typically, topical administration of drugs has been applied for the treatment of airway-, eye, sexual dysfunction and skin disorders. In addition, local injection/infiltration into diseased tissues further extend the potential medical use of locally applied ROCK inhibitors. Given certain criteria are fulfilled, these local applications allow high drug concentration to be reached in the target tissue. In addition, the incorporation of ROCK inhibitors into implants and stents can further expand the medical application towards the local treatment of CV diseases such as atherosclerosis, coronary diseases and heart failure.

Despite the fact that direct local application is preferred in medical practice, there are concerns regarding drug levels reached into the systemic circulation. For example the treatment of airway diseases by local delivery by for instance inhalation, poses the risk of systemic exposure due to large amounts entering the GI tract and/or systemic absorption through the lungs. For the treatment of eye diseases by local delivery, also significant amounts enter the GI tract and/or systemic circulation due to the low permeability of the cornea, low capacity for fluid, efficient drainage and presence of blood vessels in the eyelids. Also for dermal applications, local injections and implantable medical devices, there is a severe risk of leakage into the systemic circulation. Therefore, in addition to local application, the compounds should preferably have additional properties to avoid significant systemic exposure.

Soft drugs are biologically active compounds that are inactivated once they enter the systemic circulation. This inactivation can be achieved in the liver and/or in blood. These compounds, once applied locally to the target tissue/organ exert their desired effect locally. When they leak out of this tissue/organ into the systemic circulation, they are very rapidly inactivated. Thus, soft drugs of choice are sufficiently stable in the target tissue/organ to exert the desired biological effect, but are rapidly degraded in the liver or in the blood to biologically inactive compounds. In addition, it is highly preferable that the soft drugs of choice have retention at their biological target. This property will limit the number of applications and is highly desired to reduce the total load of drug and metabolites and in addition will significantly increase the patient compliance.

In conclusion, there is a continuing need to design and develop soft ROCK inhibitors for the treatment of a wide range of disease states. The compounds described herein and pharmaceutically acceptable compositions thereof are useful for treating or lessening the severity of a variety of disorders or conditions associated with ROCK activation. More specifically, the compounds of the invention are preferably used in the prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration and remodeling. For example, the compounds of the invention may be used in the prevention and/or treatment of diseases and disorders such as:

Eye diseases or disorders: including but not limited to retinopathy, optic neuropathy, glaucoma and degenerative retinal diseases such as macular degeneration, proliferative vitreoretinopathy, proliferative diabetic retinopathy retinitis pigmentosa and inflammatory eye diseases (such as anterior uveitis, panuveitis, intermediate uveitis and posterior uveitis), glaucoma filtration surgery failure, dry eye, allergic conjunctivitis, posterior capsule opacification, abnormalities of corneal wound healing and ocular pain.

Airway diseases; including but not limited to pulmonary fibrosis, emphysema, chronic bronchitis, asthma, fibrosis, pneumonia, cytsic fibrosis, chronic obstructive pulmonary disease (COPD); bronchitis and rhinitis and respiratory distress syndrome Throat, Nose and Ear diseases: including but not limited to sinus problems, hearing problems, toothache, tonsillitis, ulcer and rhinitis, Skin diseases: including but not limited to hyperkeratosis, parakeratosis, hypergranulosis, acanthosis, dyskeratosis, spongiosis and ulceration.

Intestinal diseases; including but not limited to inflammatory bowel disease (IBD), colitis, gastroenteritis, ileus, ileitis, appendicitis and Crohn's disease.

Cardiovascular and vascular diseases: including but not limited to, pulmonary hypertension and pulmonary vasoconstriction.

Inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis.

Neurological disorders: including but not limited to neuropathic pain. The present compounds are therefore suitable for preventing neurodegeneration and stimulating neurogeneration in various neurological disorders.

Proliferative diseases: such as but not limited to cancer of, breast, colon, intestine, skin, head and neck, nerve, uterus, kidney, lung, ovary, pancreas, prostate, or thyroid gland; Castleman disease; sarcoma; malignoma; and melanoma.

Kidney diseases: including but not limited to renal fibrosis or renal dysfunction Sexual dysfunction: is meant to include both male and female sexual dysfunction caused by a defective vasoactive response. The soft ROCK inhibitors of the present invention may also be used to treat sexual dysfunction arising from a variety of causes. For example, in an embodiment, the soft ROCK inhibitors may be used to treat sexual dysfunction associated with hypogonadism and more particularly, wherein the hypogonadism is associated with reduced levels of androgen hormones. In another embodiment, the soft ROCK inhibitors may be used to treat sexual dysfunction associated with a variety of causes including, but not limited to, bladder disease, hypertension, diabetes, or pelvic surgery. In addition, the soft ROCK inhibitors may be used to treat sexual dysfunction associated with treatment using certain drugs, such as drugs used to treat hypertension, depression or anxiety.

Bone diseases: including but not limited to osteoporosis and osteoarthritis

In addition, the compounds of the invention may be used in the prevention and/or treatment of diseases and disorders such as benign prostatic hyperplasia, transplant rejection, spasm, chronic obstructive bladder disease, and allergy.

SUMMARY OF THE INVENTION

We have surprisingly found that the compounds described herein act as inhibitors of ROCK, in particular as soft ROCK inhibitors. The compounds of the present invention are rapidly converted into functionally inactive compounds for example by carboxylic ester hydrolases (EC 3.1.1) such as cholinesterases or carboxylesterases. Carboxylic ester hydrolases (EC 3.1.1) represent a large group of enzymes involved in the degradation of carboxylic esters into alcohols and carboxylic acids. As such, enzymes displaying this catalytic activity are of potential interest for the design of soft kinase inhibitors. EC 3.1.1 includes the following sub-classes:

EC 3.1.1.1 carboxylesterase; EC 3.1.1.2 arylesterase; EC 3.1.1.3 triacylglycerol lipase; EC 3.1.1.4; phospholipase A2; EC 3.1.1.5 lysophospholipase; EC 3.1.1.6 acetylesterase; EC 3.1.1.7 acetylcholinesterase; EC 3.1.1.8 cholinesterase; EC 3.1.1.10 tropinesterase; EC 3.1.1.11 pectinesterase; EC 3.1.1.13 sterol esterase; EC 3.1.1.14 chlorophyllase; EC 3.1.1.15 L-arabinonolactonase; EC 3.1.1.17 gluconolactonase; EC 3.1.1.19 uronolactonase; EC 3.1.1.20 tannase; EC 3.1.1.21 retinyl-palmitate esterase; EC 3.1.1.22 hydroxybutyrate-dimer hydrolase; EC 3.1.1.23 acylglycerol lipase; EC 3.1.1.24 3-oxoadipate enol-lactonase; EC 3.1.1.25 1,4-lactonase; EC 3.1.1.26 galactolipase; EC 3.1.1.27 4-pyridoxolactonase; EC 3.1.1.28 acylcarnitine hydrolase; EC 3.1.1.29 aminoacyl-tRNA hydrolase; EC 3.1.1.30 D-arabinonolactonase; EC 3.1.1.31 6-phosphogluconolactonase; EC 3.1.1.32 phospholipase A1; EC 3.1.1.33 6-acetylglucose deacetylase;

EC 3.1.1.34 lipoprotein lipase; EC 3.1.1.35 dihydrocoumarin hydrolase; EC 3.1.1.36 limonin-D-ring-lactonase; EC 3.1.1.37 steroid-lactonase; EC 3.1.1.38 triacetate-lactonase; EC 3.1.1.39 actinomycin lactonase; EC 3.1.1.40 orsellinate-depside hydrolase; EC 3.1.1.41 cephalosporin-C deacetylase; EC 3.1.1.42 chlorogenate hydrolase; EC 3.1.1.43 α-amino-acid esterase; EC 3.1.1.44 4-methyloxaloacetate esterase; EC 3.1.1.45 carboxymethylenebutenolidase; EC 3.1.1.46 deoxylimonate A-ring-lactonase; EC 3.1.1.47 1-alkyl-2-acetylglycerophosphocholine esterase; EC 3.1.1.48 fusarinine-C ornithinesterase; EC 3.1.1.49 sinapine esterase; EC 3.1.1.50 wax-ester hydrolase; EC 3.1.1.51 phorbol-diester hydrolase; EC 3.1.1.52 phosphatidylinositol deacylase; EC 3.1.1.53 sialate O-acetylesterase; EC 3.1.1.54 acetoxybutynylbithiophene deacetylase; EC 3.1.1.55 acetylsalicylate deacetylase; EC 3.1.1.56 methylumbelliferyl-acetate deacetylase; EC 3.1.1.57 2-pyrone-4,6-dicarboxylate lactonase; EC 3.1.1.58 N-acetylgalactosaminoglycan deacetylase; EC 3.1.1.59 juvenile-hormone esterase; EC 3.1.1.60 bis(2-ethylhexyl)phthalate esterase; EC 3.1.1.61 protein-glutamate methylesterase; EC 3.1.1.63 11-cis-retinyl-palmitate hydrolase; EC 3.1.1.64 all-trans-retinyl-palmitate hydrolase; EC 3.1.1.65 L-rhamnono-1,4-lactonase; EC 3.1.1.66 5-(3,4-diacetoxybut-1-ynyl)-2,2'-bithiophene deacetylase; EC 3.1.1.67 fatty-acyl-ethyl-ester synthase; EC 3.1.1.68 xylono-1,4-lactonase; EC 3.1.1.70 cetraxate benzylesterase; EC 3.1.1.71 acetylalkylglycerol acetylhydrolase; EC 3.1.1.72 acetylxylan esterase; EC 3.1.1.73 feruloyl esterase; EC 3.1.1.74 cutinase; EC 3.1.1.75 poly(3-hydroxybutyrate) depolymerase; EC 3.1.1.76 poly(3-hydroxyoctanoate) depolymerase; EC 3.1.1.77 acyloxyacyl hydrolase; EC 3.1.1.78 polyneuridine-aldehyde esterase; EC 3.1.1.79 hormone-sensitive lipase; EC 3.1.1.80 acetylajmaline esterase; EC 3.1.1.81 quorum-quenching N-acyl-homoserine lactonase; EC 3.1.1.82 pheophorbidase; EC 3.1.1.83 monoterpene ε-lactone hydrolase; EC 3.1.1.84 cocaine esterase; EC 3.1.1.85 mannosylglycerate hydrolases.

Cholinesterases are enzymes that are primarily known for their role in the degradation of the neurotransmitter acetylcholine. Acetylcholinesterase (EC 3.1.1.7) is also known as Choline esterase I, true cholinesterase, RBC cholinesterase, erythrocyte cholinesterase, or acetylcholine acetylhydrolase. As suggested by some of its alternative names, acetylcholinesterase is not only found in brain, but also in the erythrocyte fraction of blood. In addition to its action on acetylcholine, acetylcholinesterase hydrolyzes a variety of acetic esters, and also catalyzes transacetylations. Acetylcholinesterase usually displays a preference for substrates with short acid chains, as the acetyl group of acetylcholine. Butyrylcholinesterase (EC 3.1.1.8) is also known as benzoylcholinesterase, choline esterase II, non-specific cholinesterase, pseudocholinesterase, plasma cholinesterase or acylcholine acylhydrolase, While being found primarily in liver, butyrylcholinesterase is also present in plasma. As indicated by some of its alternative names, it is less specific than acetylcholinesterase and will typically carry out the hydrolysis of substrates with larger acid chains (such as the butyryl group of butyrylcholine or the benzoyl group of benzolylcholine) at a faster rate than acetylcholinesterase. In addition to its action on acetylcholine, butyrylcholinesterase is known to participate in the metabolism of several ester drugs, such as procaine.

Carboxylesterases (CES) represent a multigene family and show ubiquitous expression profiles, with high levels in liver, intestine and lungs. A majority of carboxylesterases can be classified either in carboxylesterase 1 (CES 1) or carboxylesterase 2 (CES2) families. Interestingly, these different CES families show differences in tissue distribution and substrate specificity. Human CES1 is widely distributed in many tissues, but is found in low levels in the intestine. CES1 preferentially hydrolyzes esters with relatively small alcohol groups and larger acid groups. As a typical example, hCES1 preferentially catalyzes the hydrolysis of the methyl ester of cocaine. Human CES2 is predominantly found in intestine, liver and kidney. CES2 preferentially hydrolyzes esters with smaller alcohol groups, and larger acid groups. As a typical example, human CES2 catalyzes the hydrolysis of the benzoyl ester of cocaine. Another interesting observation about CES enzymes is the lack of carboxylesterase activity in human plasma. Overall, carboxylesterases can play a major role in the bioconversion of ester-containing drugs and xenobiotics.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, salt, hydrate, or solvate thereof,

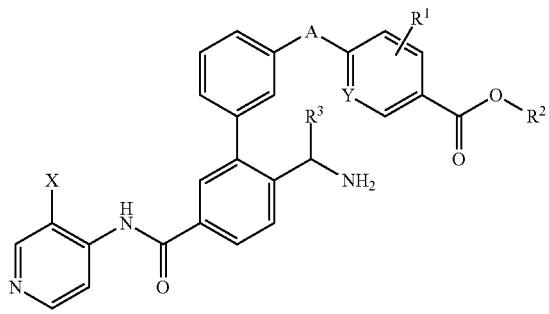

I

Wherein,
X is hydrogen or halogen;
A is —NH—C(=O)— or —C(=O)—NH—;
Y is N or C;
$R^3$ is selected from the group comprising hydrogen, $C_{1-20}$alkyl and $C_{3-15}$cycloalkyl;
$R^1$ is selected from the group comprising hydrogen, $C_{1-20}$alkyl, $C_{1-20}$alkoxy, and halogen; and
$R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, $C_{3-20}$alkynyl, $C_{3-15}$cycloalkyl, aryl, heteroaryl, and $C_{3-19}$heterocyclyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, $C_{1-6}$alkyl, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;
or $R^2$ taken together with $R^1$ forms a cyclic ester (lactone) comprising from 4 to 9 carbon atoms in the cyclic ester ring.

Viewed from a further aspect, the invention provides the use of a compound of the invention, or a composition comprising such a compound, for inhibiting the activity of at least one kinase, in vitro or in vivo.

Viewed from a further aspect, the invention provides the use of a compound of the invention, or a composition comprising such a compound, for inhibiting the activity of at least one ROCK kinase, for example ROCKII and/or ROCKI isoforms.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of at least one disease and/or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, chronic obstructive bladder disease, and allergy.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I

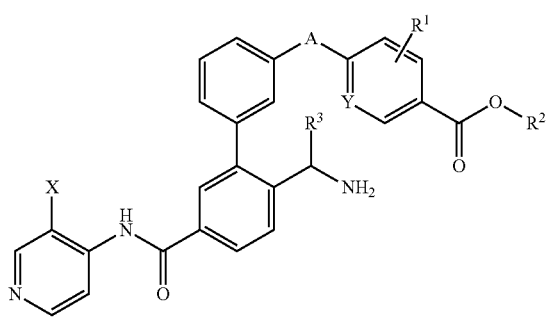

I

Wherein, X, $R^1$, A, Y, $R^2$ and $R^3$ are as defined hereinbefore, including the stereo-isomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl (also shortened as Me), ethyl, n-propyl (also shortened as nPr), i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, oxo, carbonyl, nitro, amino, amido, oxime, imino, azido, hydrazino, cyano, aryl, heteroaryl, cycloalkyl, heterocyclyl, alkylamino, alkoxy, haloalkoxy, haloalkyl, thiol, alkylthio, carboxylic acid, acylamino, alkyl esters, carbamate, thioamido, urea, sulfonamido and the like.

The term "alkylamino", as used herein refers to an amino group substituted with one or more alkyl chain(s). This definition includes quaternary ammonium derivatives.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, isopropynyl, butynyl, isobutynyl, pentynyl, hexynyl, and the like. An optionally substituted alkynyl refers to an alkynyl having optionally one or more substituents selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred.

An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2$CH_2$—*, *—CH(—$CH_2CH_3$)—*, or *—$CH_2$CH(—$CH_3$)—*. Likewise a $C_3$ cycloalkylene group may be

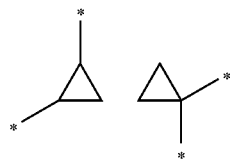

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclyl refers to a heterocyclyl having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2, 4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, arylcarbonyl, aminocarbonyl, alkylsulfoxide, —$SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl),as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl.

The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2- benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl". as used herein includes quinoxalin-2-yl, quinoxalin-5-yl, and quinoxalin-6-yl. The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl. The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl. The term "5-azaindolyl" as used herein refers to 1H-Pyrrolo[3,2-5 c]pyridinyl and includes 5-azaindol-1-yl, 5-azaindol-2-yl, 5-azaindol-3-yl, 5-azaindol-4-yl, 5-azaindol-6-yl, 5-azaindol-7-yl. The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or-5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidyl, 2-, 3-, 4-, 5- 6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1, 2-, 3-, 4-, 5-, or 7-yl, 7-azaindol-1-, 2-, 3-, 4,5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -7-yl1-, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazol-2-yl, imidazo[2,1-b][1,3]thiazol-3-yl, imidazo[2, 1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5-a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —$R^d$—$R^e$ wherein $R^d$ is alkylene or alkylene substituted by alkyl group and $R^b$ is a heterocyclyl group.

The term "carboxy" or "carboxyl" or "hydroxycarbonyl" by itself or as part of another substituent refers to the group —$CO_2H$. Thus, a carboxyalkyl is an alkyl group as defined above having at least one substituent that is —$CO_2H$.

The term "alkoxycarbonyl" by itself or as part of another substituent refers to a carboxy group linked to an alkyl radical i.e. to form $C(=O)OR^e$, wherein $R^e$ is as defined above for alkyl.

The term "alkylcarbonyloxy" by itself or as part of another substituent refers to a —O—$C(=O)R^e$ wherein $R^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above.

The term "haloalkoxy" alone or in combination refers to a group of Formula —O-alkyl wherein the alkyl group is substituted by 1, 2, or 3 halogen atoms. For example, "haloalkoxy" includes —$OCF_3$, —$OCHF_2$, —$OCH_2F$, —O—$CF_2$—$CF_3$, —O—$CH_2$—$CF_3$, —O—$CH_2$—$CHF_2$, and —O—$CH_2$—$CH_2F$.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted in Tables 1 to 11, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a further embodiment, the present invention provides compounds of formula I as described herein, wherein;

$R^3$ is selected from the group comprising hydrogen, $C_{1-6}$alkyl, and $C_{3-6}$cycloalkyl, in particular hydrogen or $C_{1-3}$alkyl; more in particular hydrogen.

In a preferred embodiment, the present invention provides compounds of formula I, wherein;

X is hydrogen or halogen; in particular halogen; more in particular fluoro;

A is —NH—C(=O)— or C(=O)—NH—;

Y is N or C;

$R^3$ is selected from the group comprising hydrogen, $C_{1-20}$alkyl, and $C_{3-15}$cycloalkyl; in particular hydrogen or $C_{1-6}$alkyl; more in particular hydrogen or $C_{1-6}$alkyl; even more in particular hydrogen;

$R^1$ is selected from the group comprising hydrogen, $C_{1-20}$alkyl, $C_{1-20}$alkoxy, and halogen; in particular hydrogen, $C_{1-6}$alkyl, and halogen; more in particular hydrogen, methyl, and halogen; and $R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, $C_{3-20}$alkynyl, $C_{3-15}$cycloalkyl, aryl, heteroaryl, and $C_{3-19}$heterocyclyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, $C_{1-6}$alkyl, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

Or $R^2$ taken together with $R^1$ form a cyclic ester (lactone) comprising from 4 to 9 carbon atoms in the cyclic ester ring.

In an even further embodiment, the present invention provides compounds of formula I as described herein, wherein;

$R^1$ is selected from the group comprising hydrogen, $C_{1-6}$alkyl, $C_{1-6}$alkoxy, and halogen; in particular hydrogen, $C_{1-6}$alkyl, and halogen; more in particular hydrogen, methyl, and halogen.

In an even further preferred embodiment, the present invention provides compounds of formula I as described herein, wherein;

$R^1$ is selected from the group comprising hydrogen, $C_{1-20}$alkyl, $C_{1-20}$alkoxy, and halogen; in particular hydrogen, methyl, and halogen; more in particular $R^1$ is methyl or fluoro; and $R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, and $C_{3-20}$alkynyl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

in particular $R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido.

or $R^2$ taken together with $R^1$ form a cyclic ester (lactone) comprising from 4 to 5 carbon atoms in the cyclic ester ring.

In a further embodiment, the present invention provides compounds of formula I as described herein, wherein;

$R^1$ is selected from the group comprising hydrogen, $C_{1-20}$alkyl, $C_{1-20}$alkoxy, and halogen; in particular hydrogen, methyl or halogen, more in particular methyl or fluoro; and $R^2$ is selected from the group consisting of $C_{1-20}$alkyl, $C_{3-20}$alkenyl, $C_{3-20}$alkynyl, and aryl; wherein said $C_{1-20}$alkyl, $C_{3-20}$alkenyl, $C_{3-20}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

in particular $R^2$ is selected from the group consisting of $C_{1-20}$alkyl, $C_{3-20}$alkenyl, $C_{3-20}$alkynyl, and aryl; wherein said $C_{1-20}$alkyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, thiol, $C_{1-20}$alkylthio, carboxylic acid, acylamino, $C_{1-20}$alkyl esters, carbamate, thioamido, urea, and sulfonamido;

or $R^2$ taken together with $R^1$ form a cyclic ester (lactone) comprising from 4 to 5 carbon atoms in the cyclic ester ring.

In another preferred embodiment, the present invention provides compounds of formula I as described herein, wherein;

$R^1$ is selected from the group comprising hydrogen, $C_{1-20}$alkyl, $C_{1-20}$alkoxy, and halogen; in particular hydrogen, methyl or halogen, more in particular methyl or fluoro; and $R^2$ is selected from the group consisting of $C_{1-6}$alkyl, $C_{3-6}$alkenyl, $C_{3-6}$alkynyl, and aryl; wherein said $C_{1-6}$alkyl, $C_{3-6}$alkenyl, $C_{3-6}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

in particular selected from the group consisting of $C_{1-6}$alkyl, $C_{3-6}$alkenyl, and $C_{3-6}$alkynyl; wherein said $C_{1-6}$alkyl, $C_{3-6}$alkenyl, and $C_{3-6}$alkynyl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

more in particular $R^2$ is $C_{1-6}$alkyl optionally substituted with a substituent selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

or $R^2$ taken together with $R^1$ form a cyclic ester (lactone) comprising from 4 to 5 carbon atoms in the cyclic ester ring.

In a particular embodiment, the present invention provides compounds of formula I as described herein, wherein;

said one or more optional substituents for $R^2$ are selected from the group consisting of halo, hydroxyl, nitro, amino, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, and halo-$C_{1-20}$alkyl; in particular from the group consisting of cyano, $C_{3-6}$cycloalkyl, $C_{3-6}$heterocyclyl, $C_{1-6}$alkoxy, di($C_{1-6}$alkyl)amino, aryl, and heteroaryl; more in particular from $C_{3-6}$heterocyclyl, and $C_{1-6}$alkoxy.

It is also an object of the invention to provide those compounds of formula I wherein one or more of the following restriction apply:

X is halogen; in particular fluoro;

A is —C(=O)—NH—;

Y is C;

$R^3$ is hydrogen;

$R^1$ is selected from the group comprising hydrogen, $C_{1-20}$alkyl, and halogen; in particular hydrogen, $C_{1-6}$alkyl, and halogen; more in particular hydrogen, methyl and fluoro $R^1$ is hydrogen;

$R^1$ is fluoro;

$R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, and $C_{3-20}$alkynyl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; in particular $R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

$R^2$ is selected from the group consisting of $C_{1-20}$alkyl, $C_{3-20}$alkenyl, $C_{3-20}$alkynyl, and aryl; wherein said $C_{1-20}$alkyl, $C_{3-20}$alkenyl, $C_{3-20}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; in particular $R^2$ is selected from the group consisting of $C_{1-20}$alkyl, $C_{3-20}$alkenyl, $C_{3-20}$alkynyl, and aryl; wherein said $C_{1-20}$alkyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;

$R^2$ is selected from the group consisting of $C_{1-6}$alkyl, $C_{3-6}$alkenyl, $C_{3-6}$alkynyl, and aryl; wherein said $C_{1-6}$alkyl, $C_{3-6}$alkenyl, $C_{3-6}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; in particular selected from the group consisting of $C_{1-6}$alkyl, $C_{3-6}$alkenyl, and $C_{3-6}$alkynyl; wherein said $C_{1-6}$alkyl, $C_{3-6}$alkenyl, and $C_{3-6}$alkynyl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; more in particular $R^2$ is $C_{1-6}$alkyl optionally substituted with a substituent selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; even more in particular $R^2$ is $C_{1-6}$alkyl.

said one or more optional substituents for $R^2$ are selected from the group consisting of halo, hydroxyl, nitro, amino, cyano, aryl, heteroaryl, $C_{3-15}$cycloalkyl, $C_{3-19}$heterocyclyl, $C_{1-20}$alkylamino, di($C_{1-20}$alkyl) amino, $C_{1-20}$alkoxy, and halo-$C_{1-20}$alkyl; in particular from the group consisting of cyano, $C_{3-6}$cycloalkyl, $C_{3-6}$heterocyclyl, $C_{1-6}$alkoxy, di($C_{1-6}$alkyl)amino, aryl, and heteroaryl; more in particular from $C_{3-6}$heterocyclyl, and $C_{1-6}$alkoxy; said one or more optional substituents for $R^2$ are selected from $C_{3-19}$heterocyclyl and $C_{1-20}$alkoxy; more in particular from oxolanyl and methoxy;

$R^1$ and $R^2$ taken together form a cyclic ester comprising 4 carbon atoms in the cyclic ester ring.

In another particular embodiment, the present invention provides a compound selected from the group consisting of:

methyl 4-({3-[2-(aminomethyl)-5-[(3-fluoropyridin-4-yl)carbamoyl]phenyl]phenyl}amido)benzoate;

methyl 4-({3-[2-(aminomethyl)-5-[(3-fluoropyridin-4-yl)carbamoyl]phenyl]phenyl}amido)-3-fluorobenzoate;

methyl 4-({3-[2-(aminomethyl)-5-[(3-fluoropyridin-4-yl)carbamoyl]phenyl]phenyl}amido)-2-fluorobenzoate;

propyl 4-({3-[2-(aminomethyl)-5-[(3-fluoropyridin-4-yl)carbamoyl]phenyl]phenyl}amido)-3-fluorobenzoate;

methyl 4-({3-[2-(aminomethyl)-5-[(3-fluoropyridin-4-yl)carbamoyl]phenyl]phenyl}amido)-2-methylbenzoate;

propyl 4-({3-[2-(aminomethyl)-5-[(3-fluoropyridin-4-yl)carbamoyl]phenyl]phenyl}amido)-2-methylbenzoate;

methyl 4-({3-[2-(aminomethyl)-5-[(3-fluoropyridin-4-yl)carbamoyl]phenyl]phenyl}carbamoyl)benzoate;

methyl 6-({3-[2-(aminomethyl)-5-[(3-fluoropyridin-4-yl)carbamoyl]phenyl]phenyl}carbamoyl)pyridine-3-carboxylate;

2-methoxyethyl 4-({3-[2-(aminomethyl)-5-[(3-fluoropyridin-4-yl)carbamoyl]phenyl]phenyl}amido)benzoate;

oxolan-2-ylmethyl 4-({3-[2-(aminomethyl)-5-[(3-fluoropyridin-4-yl)carbamoyl]phenyl]phenyl}amido)benzoate;

4-(aminomethyl)-N-(3-fluoropyridin-4-yl)-3-{3-[(1-oxo-1,3-dihydro-2-benzofuran-5-yl)carbamoyl]phenyl}benzamide; and N-{3-[2-(aminomethyl)-5-[(3-fluoropyridin-4-yl)carbamoyl]phenyl]phenyl}-1-oxo-1,3-dihydro-2-benzofuran-5-carboxamide.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as kinase inhibitors, either in vitro or in vivo, more in particular for the inhibition of at least one ROCK kinase, selected from ROCKI and ROCKII, in particular soft ROCK inhibitors. Accordingly the present invention provides the compounds as defined herein, or a composition comprising said compound(s) for use as a medicine.

The present invention further provides the use of a compound as defined hereinbefore or the use of a composition comprising said compound, as a human or veterinary medicine, in particular for prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration, and remodeling.

In a further embodiment, the invention provides the use of a compound as defined hereinbefore, or the use of a composition comprising said compound in the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, hypertension, chronic obstructive bladder disease, and allergy.

In a preferred embodiment, the invention provides the use of a compound as defined hereinbefore or the use of a composition comprising said compound in the prevention and/or treatment of eyes diseases including but not limited to retinopathy, optic neuropathy, glaucoma and degenerative retinal diseases such as macular degeneration, retinitis pigmentosa and inflammatory eye diseases (such as anterior uveitis, panuveitis, intermediate uveitis and posterior uveitis), and/or for preventing, treating and/or alleviating complications and/or symptoms associated therewith.

In another embodiment, the invention provides the use of a compound as defined hereinbefore or the use of a composition comprising said compound in the prevention and/or treatment of airway diseases; including but not limited to pulmonary fibrosis, emphysema, chronic bronchitis, asthma, fibrosis, pneumonia, cystic fibrosis, chronic obstructive pulmonary disease (COPD); bronchitis and rhinitis and respiratory distress syndrome, and/or for preventing, treating and/or alleviating complications and/or symptoms associated therewith.

In a further embodiment, the invention provides the use of a compound as defined hereinbefore or the use of a composition comprising said compound in the prevention and/or treatment of cardiovascular and vascular diseases: including but not limited to pulmonary hypertension and pulmonary vasoconstriction, and/or for preventing, treating and/or alleviating complications and/or symptoms associated therewith and/or alleviating complications and/or symptoms associated therewith.

In a further embodiment, the invention provides the use of a compound as defined hereinbefore or the use of a composition comprising said compound in the prevention and/or treatment of throat, nose and ear diseases: including but not limited to sinus problems, hearing problems, toothache, tonsillitis, ulcer and rhinitis, In a further embodiment, the invention provides the use of a compound as defined hereinbefore or the use of a composition comprising said compound in the prevention and/or treatment of skin diseases: including but not limited to hyperkeratosis, parakeratosis, hypergranulosis, acanthosis, dyskeratosis, spongiosis and ulceration.

In a further embodiment, the invention provides the use of a compound as defined hereinbefore or the use of a composition comprising said compound in the prevention and/or treatment of intestinal diseases: including but not limited to inflammatory bowel disease (IBD), colitis, gastroenteritis, ileus, ileitis, appendicitis and Crohn's disease.

In yet another embodiment, the invention provides the use of a compound as defined hereinbefore or the use of a composition comprising said compound in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides the use of a compound as defined hereinbefore or the use of a composition comprising said compound in the prevention, treatment and/or management of neurological and CNS disorders: including but not limited to neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides the use of a compound as defined hereinbefore or the use of a composition comprising said compound in the prevention and/or treatment of proliferative diseases: such as but not limited to cancer of breast, colon, intestine, skin, head and neck, nerve, uterus, kidney, lung, ovary, pancreas, prostate, or thyroid gland; Castleman disease; sarcoma; malignoma; and melanoma; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of kidney diseases: including but not limited to renal fibrosis or renal dysfunction; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety.

In another embodiment, the invention provides the use of a compound as defined hereinbefore or the use of a composition comprising said compound in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diseases and disorders such as benign prostatic hyperplasia, transplant rejection, spasm, chronic obstructive bladder disease, and allergy, and/or for preventing, treating and/or alleviating complications and/or symptoms associated therewith.

In a preferred embodiment the present invention provides the use of a compound as defined hereinbefore or the use of a composition comprising said compound in the prevention and/or treatment of eye diseases.

Method of Treatment

The present invention further provides a method for the prevention and/or treatment of at least one disease or disorder selected from the group comprising eye diseases; airway diseases; cardiovascular and vascular diseases; inflammatory diseases; neurological and CNS disorders: proliferative diseases; kidney diseases; sexual dysfunction; bone diseases; benign prostatic hyperplasia; transplant rejection; spasm; hypertension; chronic obstructive bladder disease; and allergy; said method comprising administering to a subject in need thereof a therapeutic effective amount of a compound or a composition as defined herein.

In a preferred embodiment, the invention provides a method for the prevention and/or treatment of eye diseases including but not limited to retinopathy, optic neuropathy, glaucoma and degenerative retinal diseases such as macular degeneration, retinitis pigmentosa and inflammatory eye diseases (such as anterior uveitis, panuveitis, intermediate uveitis and posterior uveitis), said method comprising administering to a subject in need thereof a therapeutic effective amount of a compound or a composition as defined herein.

In another embodiment, the invention provides a method for the prevention and/or treatment of airway diseases including but not limited to pulmonary fibrosis, emphysema, chronic bronchitis, asthma, fibrosis, pneumonia, cystic fibrosis, chronic obstructive pulmonary disease (COPD) bronchitis, rhinitis, and respiratory distress syndrome; said method comprising administering to a subject in need thereof a therapeutic effective amount of a compound or a composition as defined herein.

In another embodiment, the invention provides a method for the prevention and/or treatment of cardiovascular and vascular diseases: including but not limited to pulmonary hypertension and pulmonary vasoconstriction; said method comprising administering to a subject in need thereof a therapeutic effective amount of a compound or a composition as defined herein.

In another embodiment, the invention provides a method for the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis; said method comprising administering to a subject in need thereof a therapeutic effective amount of a compound or a composition as defined herein.

In another embodiment, the invention provides a method for the prevention and/or treatment of neurological and CNS disorders: including but not limited to neuropathic pain. The present compounds are therefore suitable for preventing neurodegeneration and stimulating neurogeneration in various neurological disorders; said method comprising administering to a subject in need thereof a therapeutic effective amount of a compound or a composition as defined herein.

In another embodiment, the invention provides a method for the prevention and/or treatment of proliferative diseases: such as but not limited to cancer of breast, colon, intestine, skin, head and neck, nerve, uterus, kidney, lung, liver, ovary, pancreas, prostate, or thyroid gland; Castleman disease; leukemia; sarcoma; lymphoma; malignoma; and melanoma; said method comprising administering to a subject in need thereof a therapeutic effective amount of a compound or a composition as defined herein.

In another embodiment, the invention provides a method for the prevention and/or treatment of kidney diseases: including but not limited to renal fibrosis or renal dysfunction; said method comprising administering to a subject in need thereof a therapeutic effective amount of a compound or a composition as defined herein.

In another embodiment, the invention provides a method for the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety; said method comprising administering to a subject in need thereof a therapeutic effective amount of a compound or a composition as defined herein.

In another embodiment, the invention provides a method for the prevention and/or treatment of bone diseases: including but not limited to osteoporosis and osteoarthritis; said method comprising administering to a subject in need thereof a therapeutic effective amount of a compound or a composition as defined herein.

In another embodiment, the invention provides a method for the prevention and/or treatment of diseases and disorders such as benign prostatic hyperplasia, transplant rejection, spasm, chronic obstructive bladder disease, and allergy; said method comprising administering to a subject in need thereof a therapeutic effective amount of a compound or a composition as defined herein.

In a preferred embodiment, the invention provides a method for the prevention and/or treatment of eye diseases; said method comprising administering to a subject in need thereof a therapeutic effective amount of a compound or a composition as defined herein.

In the invention, particular preference is given to compounds of Formula I or any subgroup thereof that in the inhibition assay for ROCK described below inhibit ROCK with an $IC_{50}$ value of less than 10 µM, preferably less than 1 µM, even more preferably less than 0.1 µM.

Said inhibition may be effected in vitro and/or in vivo, and when effected in vivo, is preferably effected in a selective manner, as defined above.

The term "ROCK-mediated condition" or "disease", as used herein, means any disease or other deleterious condition in which is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Generally, for pharmaceutical use, the compounds of the invention may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intramuscular or subcutaneous injection), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propyl hydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

For ophthalmic application, solutions, gels, tablets and the like are often prepared using a physiological saline solution, gel or excipient as a major vehicle. Ophthalmic formulations should preferably be prepared at a comfortable pH with an appropriate buffer system.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions.

The compounds can be administered by a variety of routes including the oral, rectal, ocular, transdermal, subcutaneous, intramuscular or intranasal routes, depending mainly on the specific preparation used and the condition to be treated or prevented. The at least one compound of the invention will generally be administered in an "effective amount", by which is meant any amount of a compound of the Formula I or any subgroup thereof that, upon suitable administration, is sufficient to achieve the desired therapeutic or prophylactic effect in the individual to which it is administered.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Physicochemical Properties of the Compounds

A.1. Compound Purity

Unless indicated otherwise, the purity of the compounds was confirmed by liquid chromatography/mass spectrometry (LC/MS).

A.2. Attribution of the Configuration:

The Cahn-Ingold-Prelog system was used to attribute the absolute configuration of chiral center, in which the four groups on an asymmetric carbon are ranked to a set of sequences rules. Reference is made to Cahn; Ingold; Prelog *Angew. Chem. Int. Ed. Engl.* 1966, 5, 385-415.

A.3. Stereochemistry:

It is known by those skilled in the art that specific enantiomers (or diastereoisomers) can be obtained by different methods such as, but not limited to chiral resolution (for example, salts formed with optically active acids or bases may be used to form diastereoisomeric salts that can facilitate the separation of optically active isomers of the compounds of Formula I or any subgroup thereof), assymetric synthesis or preparative chiral chromatography (using different column such as Chiralcel OD-H (tris-3,5-dimethylphenylcarbamate, 46×250 or 100×250 mm, 5 μm), Chiralcel OJ (tris-methyl-benzoate, 46×250 or 100×250 mm, 5 μm), Chiralpak AD (tris-3,5-dimethylphenylcarbamate, 46×250 mm, 10 μm) and Chiralpak AS (tris-(S)-1-phenylethylcarbamate, 46×250 mm, 10 μm) from Chiral Technologies Europe (Illkirch, France)). Whenever it is convenient, stereoisomers can be obtained starting from commercial materials with known configuration (such compounds include aminoacid for instance).

B. Compound Synthesis

B.1. Compounds of the Invention

The compounds of the invention can be made according to the following general procedures:

ferent methods such as flash chromatography eluted for instance with DCM/EtOAc or precipitation in a solvent (e.g DCM or water) to give the expected product as a white powder.

Reaction b: To a solution or suspension of the ester intermediate in an organic solvent (e.g THF, Dioxane or Acetonitrile) was added dropwise an aqueous solution of an appropriate base such as LiOH. The resulting mixture was stirred at

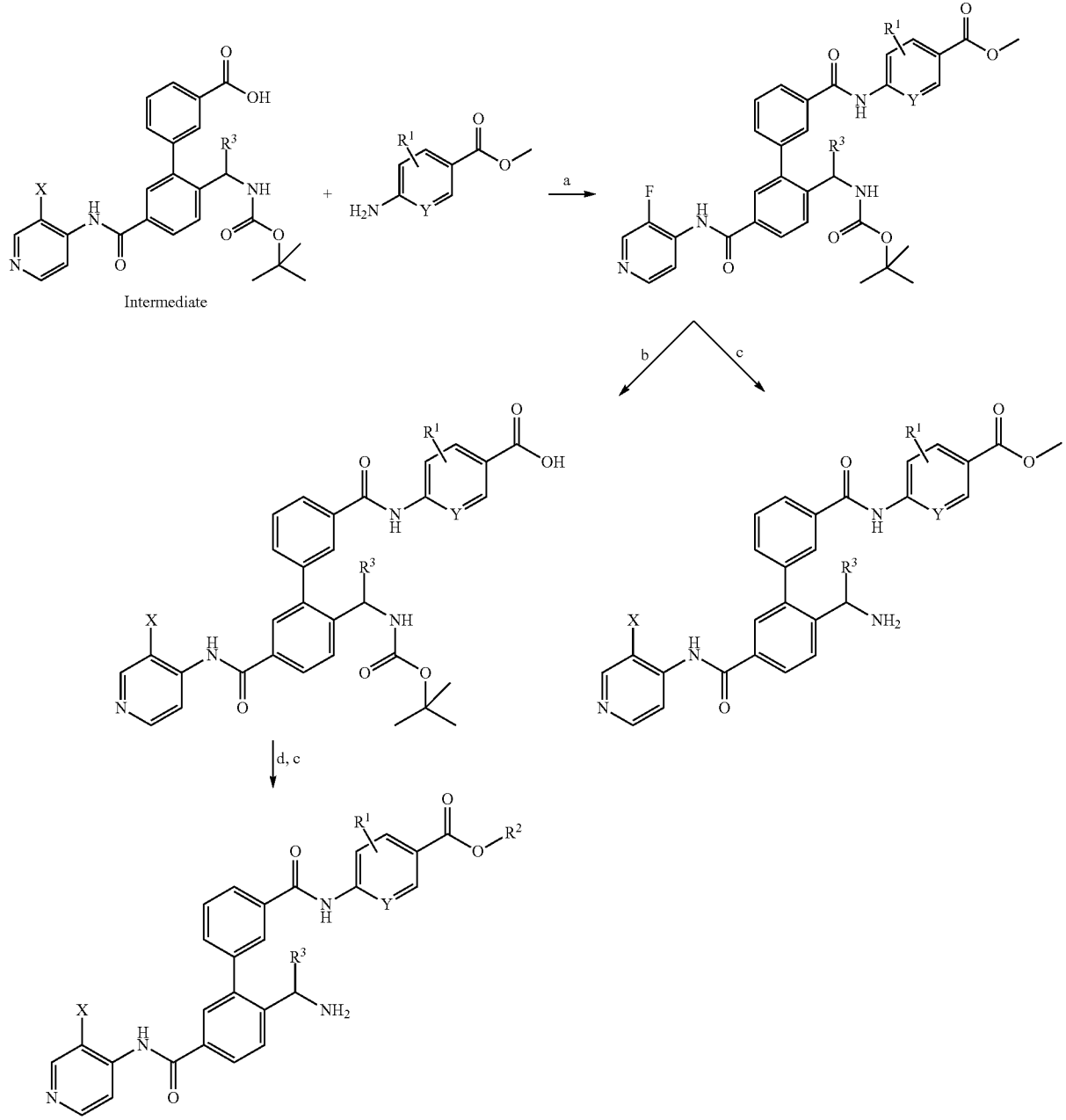

Reaction a: To a solution or suspension of the carboxylic acid intermediate in an organic solvent such as DMF or DCM at room temperature were added an appropriate coupling reagent (e.g TBTU/HOBt, HATU or T3P) and a base such as DIEA or DMAP. After 5 min the selected amine was added and the mixture stirred at the appropriate temperature (e.g rt or 60° C.) until completion of the reaction. After an appropriate work up, the residue could be purified following different methods such as flash chromatography eluted for room temperature until completion of the reaction. Then the reaction mixture was acidified until pH 4 using an appropriate acid such as HCl (0.5M in water) or KHSO4 (0.5M in water). The white suspension was collected by filtration, washed with water and an appropriate organic solvent such as AcOEt or DCM, and dried under vacuum to give the expected product as a white powder.

Reaction c: Through a solution or suspension of the Boc-protected amine in an organic solvent (e.g DCM, AcOEt, diethyl ether or Dioxane) was bubbled HCl (gas) at room temperature for 5 to 10 min. The resulting mixture was stirred at an appropriate temperature (e.g 0° C. or rt) until completion of the reaction. Then the white suspension was collected by filtration, washed with an organic solvent such as diethyl ether and dried under vacuum to give the HCl salt of the expected product as a white powder.

Reaction d: To a solution or suspension of the carboxylic acid intermediate in an organic solvent (e.g THF, DMF or DCM) at room temperature were added an appropriate coupling reagent (e.g TBTU/HOBt, HATU, DIC or T3P) and a base such as DIEA or DMAP. After 5 min the selected alcohol was added and the mixture stirred at the appropriate temperature (e.g rt or 60° C.) until completion of the reaction. After an appropriate work up, the residue was purified by flash chromatography using an appropriate eluent such as DCM/EtOAc or Heptane/EtOAc to give the expected product as a white powder.

If A=—NHC(O)—, the final compounds can be made from the required aniline intermediate and the appropriate carboxylic acid, following similar protocols.

For the preparation of the required intermediate(s), reference is made to the PCT application WO2011/107608.

In the table that is set forth below, exemplary compounds of the invention are set out in tabulated form. In this table, an arbitrarily assigned compound number and structural information are set out.

TABLE 1

| # | X | A | Y | 1 ($R^1$) | 2 ($R^1$) | $R^2$ | $R^3$ |
|---|---|---|---|---|---|---|---|
| 1 | F | —C(O)NH— | C | —H | | —Me | —H |
| 2 | F | —C(O)NH— | C | —F | | —Me | —H |
| 3 | F | —C(O)NH— | C | | —F | —Me | —H |
| 4 | F | —C(O)NH— | C | —F | | —nPr | —H |
| 5 | F | —C(O)NH— | C | | —Me | —Me | —H |
| 6 | F | —C(O)NH— | C | | —Me | —nPr | —H |
| 7 | F | —NHC(O)— | C | —H | | —Me | —H |
| 8 | F | —NHC(O)— | N | —H | | —Me | —H |
| 9 | F | —C(O)NH— | C | —H | | —(CH$_2$)$_2$—OMe | —H |
| 10 | F | —C(O)NH— | C | —H | | | —H |

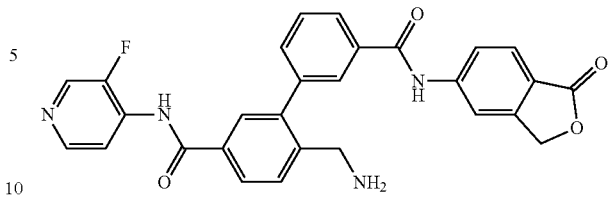

Compound 11

Compound 11 is obtained by first coupling the Intermediate carboxylic acid (as described in the general scheme/Intermediate described in WO2011/107608) with the corresponding commercially available lactone and then removing Boc protection as described in the general scheme (step c).

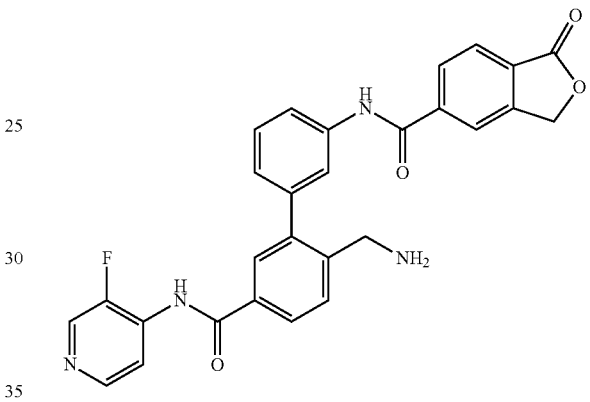

Compound 12

Compound 12 is obtained by first coupling the Intermediate aniline (as described in WO2011/107608) with the corresponding commercially available lactone and then removing Boc protection as described in the general scheme (step c).

C. In Vitro and In Vivo Assays
C.1. ROCK Inhibitory Activity Screening
C.1.1. Kinase Inhibition (ROCKI or ROCKII)

On-target activity against ROCK was measured in a biochemical assay, using the following reagents: Base Reaction buffer; 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO. Required cofactors are added individually to each kinase reaction. The reaction procedure first involved the preparation of a peptide substrate in a freshly prepared reaction buffer. Required cofactors were then added to the substrate solution. ROCK (1 nM final concentration) was then delivered to the substrate solution. After gentle mix, DMSO solutions of the test compounds were added to the enzyme. Substrate mix $^{33}$P-ATP (specific activity 0.01 μCi/μl final) was then delivered into the reaction mixture to initiate the reaction. The kinase reaction was incubated for 120 min. at room temperature. Reactions were then spotted onto P81 ion exchange paper (Whatman #3698-915). Filters were washed extensively in 0.1% Phosphoric acid. A radiometric count was then performed and IC$_{50}$ values were subsequently determined.

When evaluated under such conditions, compounds of the invention inhibit ROCK2 with an IC$_{50}$<100 nM.

C.1.2. Myosin Light Chain Phosphorylation Assay

Rat smooth muscle cell line A7r5 is used. The endogenous expression of ROCK results in a constitutive phosphorylation of the regulatory myosin light chain at T18/S19. A7r5 cells were plated in DMEM supplemented with 10% FCS in multiwall cell culture plates. After serum starvation overnight, cells were incubated with compounds in serum-free medium.

Quantification of MLC-T18/S19 phosphorylation is assessed in 96 well-plates via ELISA using a phspho-MLC-T18/S19 specific antibody and a secondary detection antibody. Raw data were converted into percent substrate phosphorylation relative to high controls, which were set to 100%. $IC_{50}$ values were determined using GraphPad Prism 5.01 software using a nonlinear regression curve fit with variable hill slope. The $EC_{50}$ values are below 500 nM for the compounds of the invention.

C.2. Pharmacological Characterization

C.2.1. Stability Assay in Human Hepatocytes.

Compounds are incubated at a concentration of 1 µM with human hepatocytes (2 $10^6$ cells/ml in buffer solution). At fixed time points (ex: 1, 30, 60 & 120 minutes), an incubation mixture (200 µl) is cooled down on ice and 100 µl of acetonitrile is added. After vortex-mixing, the sample is centrifuged for 5 minutes at 16000 rpm. The remnant of compound in each sample is determined by LC-PDA-MS/MS analysis and half-life of the compound is subsequently calculated. Formation of the acid metabolite resulting from ester hydrolysis can be performed simultaneously. Peak areas for appearance of the acid are first recorded, and the corresponding concentrations are then back-calculated from calibration curve.

When evaluated under such conditions, compounds of the invention are rapidly degraded in the corresponding acid (primary metabolite). For instance, compound 1 has a $t_{1/2}$ of 14 minutes, as illustrated in table in Table 2:

TABLE 2

| Time (min) | Cpd 1 (% remaining) | Acid (corresponding %) |
|---|---|---|
| 1 | 100.0 | 0.9 +/− 0.9 |
| 30 | 16.0 +/− 0.4 | 91.7 +/− 2.9 |
| 60 | 4.8 +/− 0.1 | 99.7 +/− 0.8 |
| 120 | 2.4 +/− 1.3 | 99.3 +/− 0.8 |

C.2.2. Stability Assay in Rabbit Aqueous or Vitreous Humor

Compounds are incubated at a concentration of 1 µM in rabbit aqueous humor (AH) or rabbit vitreous (VH). Samples are taken at fixed time points and the remnant of compound is determined by LC-MS/MS after protein precipitation. Half-life values for compounds of the invention are provided in table 3.

TABLE 3

| # Cpd | t½ Rabbit AH (min) | t½ Rabbit VH (min) |
|---|---|---|
| 1 | >60 | >60 |
| 2 | >60 | >60 |
| 3 | >60 | >60 |
| 4 | >60 | >60 |
| 5 | >60 | >60 |
| 6 | >60 | >60 |
| 7 | >60 | >60 |
| 8 | >60 | >60 |
| 9 | >60 | >60 |
| 10 | >60 | >60 |

C.2.3. Pharmacokinetics After Intravenous and Oral Administration in Mice.

The bioavailability of compound 1 was evaluated after intravenous and oral dosing in male CD-1 mice. The compound was dosed at 0.1 mg/kg intravenously and 1 mg/kg orally. Plasma levels were determined by LC-MS/MS and pharmacokinetic parameters were estimated by a non-compartmental model using WinNonlin v5.2.1 software.

After intravenous dosing of compound 1 at 0.1 mg/kg, $C_{max}$ of 16.3 ng/mL was reached. The clearance and volume of distribution were 15.4 L/hr/kg and 100 L/kg, respectively. The intravenous exposure as measured by $AUC_{last}$ was found to be 4.82±0.276 hr*ng/mL. The corresponding metabolite was detectable till 1 hour post dose with maximum concentration of 16.3 ng/mL. Metabolite had 1.47-fold higher exposure (7.10±0.920 hr*ng/mL) compared to parent compound. Following oral dosing of Compound 1 at 1 mg/kg, a $C_{max}$ of 22.4±22 ng/mL, was observed at 15 minutes post dose. $AUC_{last}$ was found to be 6.20±5.50 hr*ng/mL. The percent oral bioavailability was found to be 12.9%. Following oral dosing of Compound 1, its metabolite was detectable at 15 min only with $C_{max}$ of 4.53±3.83 ng/mL. These data confirm that Compound 1 is rapidly metabolized and excreted from the body very rapidly.

The invention claimed is:

1. A compound of Formula I or a stereoisomer, tautomer, racemic, or salt thereof,

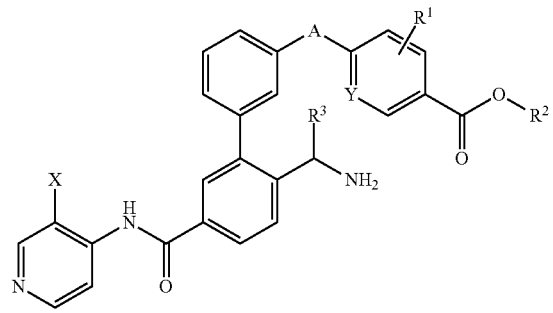

I

Wherein,
X is hydrogen or halogen;
A is —NH—C(=O)— or —C(=O)—NH—;
Y is N or C;
$R^3$ is selected from the group consisting of hydrogen, $C_{1-20}$alkyl and $C_{3-15}$cycloalkyl;
$R^1$ is selected from the group consisting of hydrogen, $C_{1-20}$alkyl, $C_{1-20}$alkoxy, and halogen; and
$R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, $C_{3-20}$alkynyl, $C_{3-15}$cycloalkyl, aryl, heteroaryl, and $C_{3-19}$heterocyclyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, $C_{1-6}$alkyl, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;
or $R^2$ taken together with $R^1$ forms a cyclic ester (lactone) comprising from 4 to 9 carbon atoms in the cyclic ester ring.

2. The compound according to claim 1 wherein $R^3$ is selected from the group consisting of hydrogen, $C_{1-6}$alkyl, and $C_{3-6}$cycloalkyl.

3. The compound according to claim 1 wherein
X is halogen;
A is —NH—C(=O)— or —C(=O)—NH—;
Y is N or C;
$R^3$ is selected from the group consisting of hydrogen, $C_{1-20}$alkyl, and $C_{3-15}$cycloalkyl; $R^1$ is selected from the group consisting of hydrogen, $C_{1-20}$alkyl, $C_{1-20}$alkoxy, and halogen; and $R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, $C_{3-20}$alkynyl, $C_{3-15}$cycloalkyl, aryl, heteroaryl, and $C_{3-19}$heterocyclyl is optionally substituted with one or more substituents selected from the group consisting of halo, hydroxyl, oxo, carbonyl, amino, amido, cyano, aryl, heteroaryl, $C_{3-15}$cycloalkyl, $C_{3-19}$heterocyclyl, $C_{1-20}$alkylamino, $C_{1-6}$alkyl, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;
or $R^2$ taken together with $R^1$ form a cyclic ester (lactone) comprising from 4 to 9 carbon atoms in the cyclic ester ring.

4. The compound according to claim 1, wherein $R^1$ is selected from the group consisting of hydrogen, $C_{1-6}$alkyl, $C_{1-6}$alkoxy, and halogen.

5. The compound according to claim 1, wherein;
$R^1$ is selected from the group consisting of hydrogen, $C_{1-20}$alkyl, $C_{1-20}$alkoxy, and halogen; and
$R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;
or $R^2$ taken together with $R^1$ form a cyclic ester (lactone) comprising from 4 to 5 carbon atoms in the cyclic ester ring.

6. The compound according to claim 1, wherein:
X is halogen;
A is —C(=O)—NH—;
Y is C;
$R^3$ is hydrogen;
$R^1$ is selected from the group consisting of hydrogen, $C_{1-20}$alkyl, and halogen; or
$R^1$ is hydrogen; or
$R^1$ is fluoro;
$R^2$ is selected from the group consisting of $C_{1-20}$alkyl, $C_{3-20}$alkenyl, $C_{3-20}$alkynyl, $C_{3-15}$cycloalkyl, aryl, heteroaryl, and $C_{3-19}$heterocyclyl; wherein said $C_{1-20}$alkyl, $C_{3-20}$alkenyl, and $C_{3-20}$alkynyl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; or $R^2$ is selected from the group consisting of $C_{1-20}$alkyl, $C_{3-20}$alkenyl, $C_{3-20}$alkynyl, and aryl; wherein said $C_{1-20}$alkyl, $C_{3-20}$alkenyl, $C_{3-20}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido; or
$R^2$ is selected from the group consisting of $C_{1-6}$alkyl, $C_{3-6}$alkenyl, $C_{3-6}$alkynyl, and aryl; wherein said $C_{1-6}$alkyl, $C_{3-6}$alkenyl, $C_{3-6}$alkynyl, and aryl is optionally substituted with one or more substituents selected from the group consisting of halo, hydroxyl, oxo, carbonyl, amino, amido, cyano, aryl, heteroaryl, $C_{1-6}$alkyl, $C_{3-15}$cycloalkyl, $C_{3-19}$heterocyclyl, $C_{1-20}$alkylamino, di($C_{1-20}$alkyl)amino, $C_{1-20}$alkoxy, halo-$C_{1-20}$alkoxy, halo-$C_{1-20}$alkyl, thiol, $C_{1-20}$alkylthio, carboxylic acid, acylamino, $C_{1-20}$alkyl esters, carbamate, thioamido, urea, and sulfonamido;
said one or more optional substituents for $R^2$ are selected from the group consisting of halo, hydroxyl, nitro, amino, cyano, aryl, heteroaryl, $C_{3-15}$cycloalkyl, $C_{3-19}$heterocyclyl, $C_{1-20}$alkylamino, di($C_{1-20}$alkyl)amino, $C_{1-20}$alkoxy, and halo-$C_{1-20}$alkyl; or
said one or more optional substituents for $R^2$ are selected from $C_{3-19}$heterocyclyl and $C_{1-20}$alkoxy; or
$R^1$ and $R^2$ taken together form a cyclic ester comprising 4 carbon atoms in the cyclic ester ring.

7. The compound according to claim 1, selected from the group consisting of
methyl 4-({3-[2-(aminomethyl)-5-[(3-fluoropyridin-4-yl)carbamoyl]phenyl]phenyl}amido)benzoate;
methyl 4-({3-[2-(aminomethyl)-5-[(3-fluoropyridin-4-yl)carbamoyl]phenyl]phenyl}amido)-3-fluorobenzoate;
methyl 4-({3-[2-(aminomethyl)-5-[(3-fluoropyridin-4-yl)carbamoyl]phenyl]phenyl}amido)-2-fluorobenzoate;
propyl 4-({3-[2-(aminomethyl)-5-[(3-fluoropyridin-4-yl)carbamoyl]phenyl]phenyl}amido)-3-fluorobenzoate;
methyl 4-({3-[2-(aminomethyl)-5-[(3-fluoropyridin-4-yl)carbamoyl]phenyl]phenyl}amido)-2-methylbenzoate;
propyl 4-({3-[2-(aminomethyl)-5-[(3-fluoropyridin-4-yl)carbamoyl]phenyl]phenyl}amido)-2-methylbenzoate;
methyl 4-({3-[2-(aminomethyl)-5-[(3-fluoropyridin-4-yl)carbamoyl]phenyl]phenyl}carbamoyl)benzoate;
methyl 6-({3-[2-(aminomethyl)-5-[(3-fluoropyridin-4-yl)carbamoyl]phenyl]phenyl}carbamoyl)pyridine-3-carboxylate;
2-methoxyethyl 4-({3-[2-(aminomethyl)-5-[(3-fluoropyridin-4-yl)carbamoyl]phenyl]phenyl}amido)benzoate;
oxolan-2-ylmethyl 4-({3-[2-(aminomethyl)-5-[(3-fluoropyridin-4-yl)carbamoyl]phenyl]phenyl}amido)benzoate;
4-(aminomethyl)-N-(3-fluoropyridin-4-yl)-3-{3-[(1-oxo-1,3-dihydro-2-benzofuran-5-yl) carbamoyl]phenyl}benzamide; and
N-{3-[2-(aminomethyl)-5-[(3-fluoropyridin-4-yl)carbamoyl]phenyl]phenyl}-1-oxo-1,3-dihydro-2-benzofuran-5-carboxamide.

8. A pharmaceutical composition comprising a compound as defined in claim 1 and one or more pharmaceutically acceptable carriers, diluents or excipients.

* * * * *